(12) United States Patent
Cozzi et al.

(10) Patent No.: US 6,753,316 B1
(45) Date of Patent: Jun. 22, 2004

(54) ACRYLOYL DERIVATIVES ANALOGOUS TO DISTAMYCIN, PROCESS FOR PREPARING THEM, AND THEIR USE AS ANTITUMOR AGENTS

(75) Inventors: Paolo Cozzi, Milan (IT); Pier Giovanni Baraldi, Ferrara (IT); Italo Beria, Villamarzana (IT); Marina Caldarelli, Milan (IT); Laura Capolongo, Milan (IT); Romeo Romagnoli, Ferrara (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/623,506

(22) PCT Filed: Mar. 17, 1999

(86) PCT No.: PCT/EP99/01822

§ 371 (c)(1),
(2), (4) Date: Sep. 19, 2000

(87) PCT Pub. No.: WO99/50265

PCT Pub. Date: Oct. 7, 1999

(30) Foreign Application Priority Data

Mar. 27, 1998 (GB) .............................................. 9806689

(51) Int. Cl.[7] .................. A61K 31/415; A61K 31/4164; A61K 38/04; C07D 403/14

(52) U.S. Cl. .............................. 514/18; 514/19; 514/20; 514/397; 514/407; 530/330; 530/331; 530/332; 548/312.4; 548/312.7; 548/313.1; 548/314.7; 548/364.1; 548/365.1

(58) Field of Search .............................. 514/18, 19, 20, 514/397, 407, 422; 530/330, 331, 332; 548/312.4, 312.7, 313.1, 314.7, 364.1, 365.1, 518

(56) References Cited

U.S. PATENT DOCUMENTS 5,175,182 A * 12/1992 Mongelli et al. ........... 514/428

FOREIGN PATENT DOCUMENTS

| WO | 95 04732 | 2/1995 |
| WO | 96 05196 | 2/1996 |
| WO | 97 43258 | 11/1997 |
| WO | 98 04524 | 2/1998 |

OTHER PUBLICATIONS

Baraldi et al Synthesis and Antitumor Activity of Novel. . . Bioorg. Med. Chem. Lett. vol. 6, No. 11, pp. 1241–1246, 1996.*

* cited by examiner

Primary Examiner—Jeffrey E. Russel

(57) ABSTRACT

Compounds which are acryloyl substituted distamycin derivatives of formula (I) wherein: n is 2, 3 or 4; m is 1 or 2; X and Y are the same or different and are selected, independently for each heterocyclic ring of the polyeterocyclic chain, from N and CH; $R_1$ and $R_2$, which are the same or different, are selected from hydrogen, halogen, and $C_1$–$C_4$ alkyl; $R_3$ is hydrogen or halogen; B is selected from (a), (b), (c), (d), (e), (f), (g) and —C≡N; wherein $R_4$, $R_5$, $R_6$, $R_7$, $R_8$, $R_{10}$, $R_{11}$, and $R_{12}$ are, independently from each other, hydrogen or $C_1$–$C_4$ alkyl; and $R_9$ is hydrogen or hydroxy, or pharmaceutically acceptable salt thereof; provided that a) at least one of $R_4$, $R_5$ and $R_6$ is alkyl b) at least one of the heterocyclic rings within the polyheterocyclic chain is other than pyrole; and c) X and Y are not both N for the same heterocyclic ring; are useful as antitumor agents.

8 Claims, No Drawings

ACRYLOYL DERIVATIVES ANALOGOUS TO DISTAMYCIN, PROCESS FOR PREPARING THEM, AND THEIR USE AS ANTITUMOR AGENTS

The present invention relates to new peptidic compounds analogous to Distamycin A, to a process for their preparation, to pharmaceutical compositions containing them and to their use as therapeutic agents.

Distamycin A is an antibiotic substance with antiviral and oncolytic properties, having a polypyrrole framework (Nature 203, 1064 (1964); J. Med. Chem. 32, 774–778 (1989)).

Several compunds analogous to Distamycin A and derivatives thereof are known in the art.

The international patent application WO 97/43258, in the name of the applicant, discloses acryloyl distamycin derivatives wherein the amidino moiety is replaced by different nitrogen-containing ending groups such as, for instance, cyanamidino, N-methylamidino, ethylguanidino, amido, amidoximo, nitrile and the like.

Distamycin derivatives wherein at least one pyrrole ring of the aforementioned polypyrrole framework is substituted by an imidazole or pyrazole ring are also reported in the literature.

See, for a general reference, Anti-Cancer Drug Design 8, 173–192 (1993); J. Am. Chem. Soc. Vol. 114, 5911–5919 (1992); Anti-Cancer Drug Design 6, 501–517 (1991); patent applications EP-A-0246868 and WO 96/05196, both in the name of the applicant.

It has now been found that a new class of distamycin derivatives as defined hereinunder, wherein at least one ring of the polypyrrole framework is other than pyrrole, the formyl group is substituted by an acryloyl moiety and the amidino group is substituted by different nitrogen-containing ending groups, shows valuable biological properties.

Therefore, the present invention provides compounds which are acryloyl substituted distamycin derivatives of formula

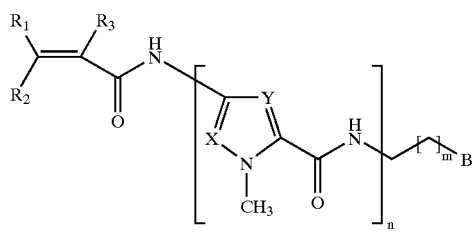

(I)

wherein:
n is 2, 3 or 4;
m is 1 or 2;
X and Y are the same or different and are selected, independently for each heterocyclic ring of the polyhetherocyclic chain, from N and CH;
$R_1$ and $R_2$, which are the same or different, are selected from hydrogen, halogen, and $C_1$–$C_4$ alkyl;
$R_3$ is hydrogen or halogen;

B is selected from

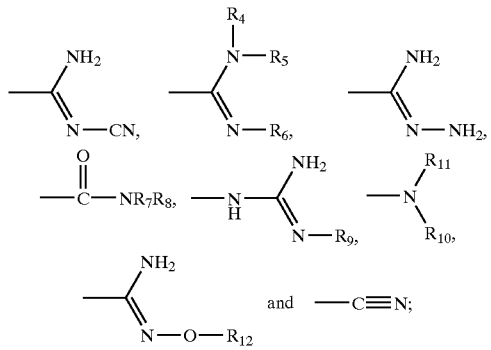

wherein $R_4$, $R_5$, $R_6$, $R_7$, $R_8$, $R_{10}$, $R_{11}$ and $R_{12}$ are, independently from each other, hydrogen or $C_1$–$C_4$ alkyl; and $R_9$ is hydrogen or hydroxy;
or a pharmaceutically acceptable salt thereof;
provided that
a) at least one of $R_4$, $R_5$ and $R_6$ is alkyl;
b) at least one of the heterocyclic rings within the polyheterocyclic chain is other than pyrrole; and
c) X and Y are not both N for the same heterocyclic ring.

The present invention includes within its scope also all the possible isomers covered by the compounds of formula (I), both separately and in admixture, as well as the metabolites and the pharmaceutically acceptable bio-precursors (otherwise known as pro-drugs) of the compounds of formula (I).

In the present description, unless otherwise specified, the term alkyl includes straight or branched alkyl, for instance $C_1$–$C_4$ alkyl such as methyl, ethyl, n-propyl, isopropyl, n-butyl, isobutyl, sec-butyl and tert-butyl; the term halogen includes fluorine, chlorine, bromine and iodine.

Preferably, the alkyl groups are selected from methyl and ethyl and the halogen atoms are selected from fluorine, chlorine or bromine.

Pharmaceutically acceptable salts of the compounds of formula (I) are the salts with pharmaceutically acceptable, inorganic or organic, acids. Examples of inorganic acids are hydrochloric, hydrobromic, sulphuric and nitric acid; examples of organic acids are acetic, propionic, succinic, malonic, citric, tartaric, methanesulfonic and p-toluenesulfonic acid.

As above reported, X and Y are selected, independently for each heterocyclic ring of the polyheterocyclic chain, between N and CH. This means that within the compounds of formula (I) and for different heterocyclic rings, X can be either N as well as CH; the same applies for Y provided that X and Y are not contemporaneously N for a single heterocycle.

Examples for the said heterocycles are pyrrole, pyrazole and imidazole.

A preferred class of compounds according to the present invention is represented by the compounds of formula (I) wherein $R_4$, $R_5$, $R_6$, $R_7$, $R_8$, $R_{10}$, $R_{11}$ and $R_{12}$ are, independently from each other, hydrogen, methyl, or ethyl.

Even more preferred are the compounds of formula (I) wherein
n is 3 or 4;
m is 1;
$R_1$ and $R_2$ are hydrogen;
$R_3$ is chlorine or bromine;

B is selected from

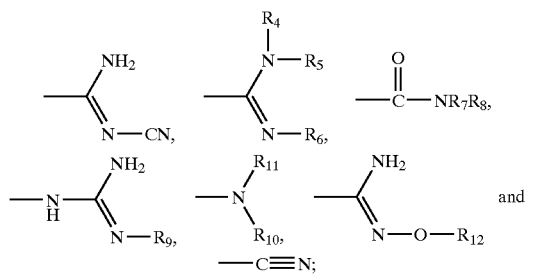

wherein $R_4$, $R_5$, $R_6$, $R_7$, $R_8$, $R_{10}$, $R_{11}$ and $R_{12}$ are, independently from each other, hydrogen or methyl; $R_9$ is hydrogen.

Another class of preferred compounds of formula (I) are those wherein the acrylamido moiety is directly linked to a pyrazole or imidazole ring.

Examples of specific compounds according to the present invention, especially in the form of salts, preferably with hydrochloric acid, are the following:

(1) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propioncyanamidine;

(2) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N-methylamidine;

(3) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-N-methylamidine;

(4) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N,N'-dimethylamidine;

(5) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-N,N'-dimethylamidine;

(6) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N,N,N'-trimethylamidine;

(7) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propionamide;

(8) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N-methylamide;

(9) 2-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)ethylguanidine;

(10) 2-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)ethylguanidine;

(11) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propyl-N,N-dimethylamine;

(12) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propionamidoxime;

(13) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propionamidoxime;

(14) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-O-methylamidoxime;

(15) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-O-methylamidoxime;

(16) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propionitrile;

(17) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propionitrile;

(18) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propioncyanamidine;

(19) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N-methylamidine;

(20) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N,N'-dimethylamidine;

(21) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N,N,N'-trimethylamidine;

(22) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido propionamide;

(23) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N-methylamide;

(24) 2-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)ethylguanidine;

(25) 2-(1-methyl-4-(1-methyl-4-(1-methyl-4-(1-methyl-4-(α-chloroacrylamido)imidazole-2-carboxamido)pyrrole-2-carboxamido)pyrrole-2-carboxamido)pyrrole-2-carboxamido)ethylguanidine;

(26) 3-(1-methyl-4-(1-methyl-4-(1-methyl-4-(1-methyl-4-(α-bromoacrylamido)imidazole-2-carboxamido)

(27) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propionamidoxime;

(28) 3-(1-methyl-4-(1-methyl-4-(1-methyl-4-(1-methyl-4-(α-chloroacrylamido)imidazole-2-carboxamido)pyrrole-2-carboxamido)pyrrole-2-carboxamido)pyrrole-2-carboxamido)propionamidoxime;

(29) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-O-methylamidoxime;

(30) 3-(1-methyl-4-(1-methyl-4-(1-methyl-4-(1-methyl-4-(α-chloroacrylamido)imidazole-2-carboxamido)pyrrole-2-carboxamido)pyrrole-2-carboxamido)pyrrole-2-carboxamido)propion-O-methylamidoxime;

(31) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido) propionitrile;

(32) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N-methylamidine;

(33) 3-(1-methyl-4-(1-methyl-4-(1-methyl-3-(1-methyl-3-(α-chloroacrylamido)pyrazole-5-carboxamido)pyrazole-5-carboxamido)pyrrole-2-carboxamido)pyrrole-2-carboxamido)propion-N-methylamidine;

(34) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N,N'-dimethylamidine;

(35) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N,N,N'-trimethylamidine;

(36) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N-methylamide;

(37) 2-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)ethylguanidine;

(38) 2-(1-methyl-4-(1-methyl-4-(1-methyl-3-(1-methyl-3-(α-chloroacrylamido)pyrazole-5-carboxamido)pyrazole-5-carboxamido)pyrrole-2-carboxamido)pyrrole-2-carboxamido)ethylguanidine;

(39) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propionamidoxime;

(40) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propionitrile;

(41) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propioncyanamidine;

(42) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propion-N-methylamide;

(43) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propion-N,N-dimethylamine;

(44) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propion-O-methylamidoxime;

(45) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propionitrile;

(46) 3-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propion-N-methylamidine;

(47) 3-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propion-N,N'-dimethylamidine;

(48) 2-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)ethylguanidine;

(49) 3-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propionamidoxime;

(50) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)imidazole-2-carboxamido)propion-N-methylamidine;

(51) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)imidazole-2-carboxamido)propionamide;

(52) 2-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)imidazole-2-carboxamido)ethylguanidine;

(53) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)imidazole-2-carboxamido)propionamidoxime;

(54) 3-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)propion-N-methylamidine;

(55) 3-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)propion-N,N'-dimethylamidine;

(56) 2-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)ethylguanidine;

(57) 3-(1-methyl-4-(1-methyl-4-(1-methyl-4-(1-methyl-3-(α-bromoacrylamido)pyrazole-5-carboxamido)

imidazole-2-carboxamido)pyrrole-2-carboxamido) pyrrole-2-carboxamido)propionamidoxime;

(58) 3-(1-methyl-4-(1-methyl-4-(1-methyl-4-(1-methyl-3-(α-bromoacrylamido)pyrazole-5-carboxamido) imidazole-2-carboxamido)pyrrole-2-carboxamido) pyrrole-2-carboxamido)propionitrile;

(59) 3-(1-methyl-4-(1-methyl-4-(1-methyl-3-(α-bromoacrylamido)pyrazole-5-carboxamido)pyrrole-2-carboxamido)pyrrole-2-carboxamido) propioncyanamidine;

(60) 3-(1-methyl-4-(1-methyl-4-(1-methyl-3-(α-bromoacrylamido)pyrazole-5-carboxamido)pyrrole-2-carboxamido)pyrrole-2-carboxamido)propion-N-methylamidine;

(61) 3-(1-methyl-4-(1-methyl-4-(1-methyl-3-(α-chloroacrylamido)pyrazole-5-carboxamido)pyrrole-2-carboxamido)pyrrole-2-carboxamido)propion-N-methylamidine;

(62) 3-(1-methyl-4-(1-methyl-4-(1-methyl-3-(α-bromoacrylamido)pyrazole-5-carboxamido)pyrrole-2-carboxamido)pyrrole-2-carboxamido)propion-N,N'-dimethylamidine,

(63) 3-(1-methyl-4-(1-methyl-4-(1-methyl-3-(α-bromoacrylamido)pyrazole-5-carboxamido)pyrrole-2-carboxamido)pyrrole-2-carboxamido)propion-N,N,N'-trimethylamidine;

(64) 3-(1-methyl-4-(1-methyl-4-(1-methyl-3-(α-bromoacrylamido)pyrazole-5-carboxamido)pyrrole-2-carboxamido)pyrrole-2-carboxamido)propionamide;

(65) 2-(1-methyl-4-(1-methyl-4-(1-methyl-3-(α-bromoacrylamido)pyrazole-5-carboxamido)pyrrole-2-carboxamido)pyrrole-2-carboxamido)ethylguanidine;

(66) 2-(1-methyl-4-(1-methyl-4-(1-methyl-3-(α-chloroacrylamido)pyrazole-5-carboxamido)pyrrole-2-carboxamido)pyrrole-2-carboxamido)ethylguanidine;

(67) 3-(1-methyl-4-(1-methyl-4-(1-methyl-3-(α-bromoacrylamido)pyrazole-5-carboxamido)pyrrole-2-carboxamido)pyrrole-2-carboxamido) propionamidoxime;

(68) 3-(1-methyl-4-(1-methyl-4-(1-methyl-3-(α-chloroacrylamido)pyrazole-5-carboxamido)pyrrole-2-carboxamido)pyrrole-2-carboxamido) propionamidoxime;

(69) 3-(1-methyl-4-(1-methyl-4-(1-methyl-3-(α-bromoacrylamido)pyrazole-5-carboxamido)pyrrole-2-carboxamido)pyrrole-2-carboxamido)propionitrile;

(70) 3-(1-methyl-4-(1-methyl-4-(1-methyl-4-(α-bromoacrylamido)imidazole-2-carboxamido)pyrrole-2-carboxamido)pyrrole-2-carboxamido) propioncianamidine;

(71) 3-(1-methyl-4-(1-methyl-4-(1-methyl-4-(α-bromoacrylamido)imidazole-2-carboxamido)pyrrole-2-carboxamido)pyrrole-2-carboxamido)propion-N-methylamidine;

(72) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N'-dimethylamidine;

(73) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N,N'-trimethylamidine;

(74) 3-(1-methyl-4-(1-methyl-4-(1-methyl-4-(α-bromoacrylamido)imidazole-2-carboxamido)pyrrole-2-carboxamido)pyrrole-2-carboxamido)propionamide;

(75) 3-(1-methyl-4-(1-methyl-4-(1-methyl-4-(α-bromoacrylamido)imidazole-2-carboxamido)pyrrole-2-carboxamido)pyrrole-2-carboxamido)propion-N-methylamide;

(76) 2-(1-methyl-4-(1-methyl-4-(1-methyl-4-(α-bromoacrylamido)imidazole-2-carboxamido)pyrrole-2-carboxamido)pyrrole-2-carboxamido) ethylguanidine;

(77) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N-dimethylamine;

(78) 3-(1-methyl-4-(1-methyl-4-(1-methyl-4-(α-bromoacrylamido)imidazole-2-carboxamido)pyrrole-2-carboxamido)pyrrole-2-carboxamido) propionamidoxime;

(79) 3-(1-methyl-4-(1-methyl-4-(1-methyl-4-(α-bromoacrylamido)imidazole-2-carboxamido)pyrrole-2-carboxamido)pyrrole-2-carboxamido)propion-O-methylamidoxime;

(80) 3-(1-methyl-4-(1-methyl-4-(1-methyl-4-(α-bromoacrylamido)imidazole-2-carboxamido)pyrrole-2-carboxamido)pyrrole-2-carboxamido)propionitrile.

The compounds of the present invention can be prepared according to one of the following processes, which comprise:

(a) reacting a compound of formula:

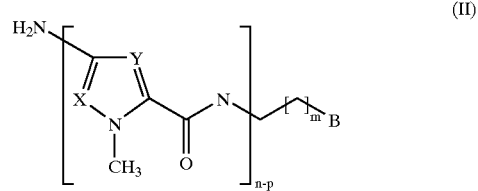

wherein n, m, X, Y and B are as defined above;
p is 0 or 1;
with a compound of formula:

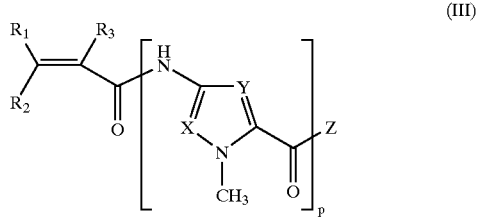

wherein $R_1$, $R_2$, $R_3$, X, Y and p are as defined above;
Z is hydroxy or a leaving group;
or:

(b) when B is equal to —C≡N, reacting a compound of formula:

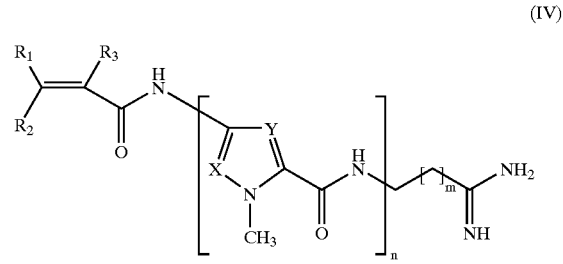

wherein n, m, $R_1$, $R_2$, $R_3$, X and Y are as defined above;
with succinic anhydride; and (c) if desired, converting a compound of formula (I) into a pharmaceutically acceptable salt thereof.

In the compounds of formula (III), Z is hydroxy or a suitable leaving group selected, for instance, among chloro, 2,4,5-trichlorophenoxy, 2,4-dinitro-phenoxy, succinimido-N-oxy, imidazolyl group, and the like.

The reaction of process (a) as above between a compound of formula (II) and a compound of formula (III) can be carried out according to known methods, for instance those described in the aforementioned EP-A-246,868 and WO 96/05196.

It is clear to the man skilled in the art that when preparing the compounds of formula (I) according to the process object of the present invention, optional amino groups, i.e. $R_{10}$ and/or $R_{11}$ of the compound of formula (II) equal to hydrogen, need to be properly protected according to conventional techniques, so as to avoid unwanted side reactions.

Likewise, the conversion of the said protected amino group into the free amine may be carried out according to known procedures. See, for a general reference, J. Org. Chem. 43, 2285, (1978); J. Org. Chem. 44, 811 (1979); J. Am. Chem. Soc. 78, 1359 (1956); Ber. 65, 1192 (1932); and J. Am Chem. Soc. 80, 1154, (1958).

The compounds of formula (II) may be prepared by converting the compounds of formula (V)

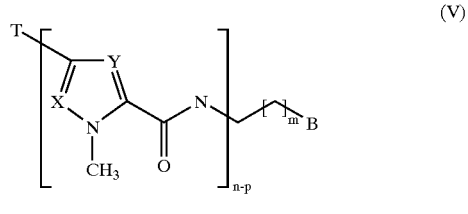

(V)

wherein T is a nitro group or an amino group properly protected with a group such as, for instance, t-butyloxycarbonyl, triphenylmethyl or, preferably, carbobenzyloxy or formyl; X, Y, B, n, m and p are as defined above; into the desired amino derivative of formula (II).

The conversion of the nitro group into amino group may be carried out according to known procedures such as, for instance, hydrogenation under hydrogen pressure in the presence of suitable catalysts, e.g., palladium on charcoal, into a suitable solvent such as dioxane, methanol, ethanol and mixtures thereof, at room temperature.

The compounds of formula (V) wherein B is other than

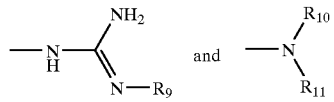

can be obtained, in their turn, from the compounds of formula:

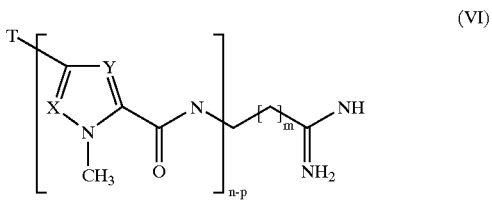

(VI)

wherein T, X, Y, n, p and m are as defined above; by using:
(i) $H_2N$—CN, so obtaining a compound of formula (V) having B equal to:

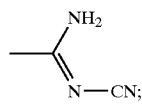

(ii) $H_2N$—$OR_{12}$ wherein $R_{12}$ has the above reported meanings, so obtaining a compound of formula (V) having B equal to:

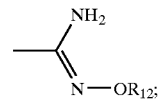

(iii) $H_2N$—$NH_2$, so obtaining a compound of formula (V) having B equal to:

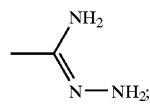

(iv) $HNR_4R_5$, so obtaining a compound of formula (V) having B equal to:

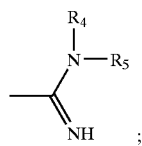

and then optionally with $H_2NR_6$, so obtaining a compound of formula (V) having B equal to:

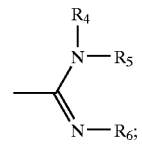

wherein $R_4$, $R_5$, and $R_6$ are as defined above;
(v) succinic anhydride, so obtaining a compound of formula (V) having B equal to —C≡N;
(vi) water in an alkaline medium, so obtaining a compound of formula (V) having B equal to —CO—$NR_7R_8$ wherein $R_7$ and $R_8$ are both hydrogen;
(vii) $HNR_7R_8$, so obtaining a compound of formula (V) having B equal to:

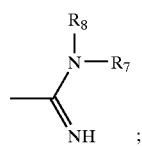

and then with water in an alkaline medium, so obtaining a compound of formula (V) having B equal to —CO—$NR_7R_8$, wherein $R_7$ and $R_8$ are as defined above.

The reaction between a compound of formula (VI) and one of the reactants as set forth in points (i)–(vii) as above can be carried out according to known methods, for instance those reported in WO97/43258; Chem. Revs. 1961; 155; J.

Med. Chem. 1984, 27, 849–857; Chem. Revs. 1970, 151; and "The Chemistry of Amidines and Imidates", edited by S. Patai, John Wiley & Sons, N.Y. (1975).

Alternatively, the compounds of formula (V) wherein B is other than

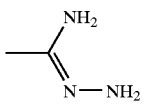

can be prepared from a compound of formula:

(VII)

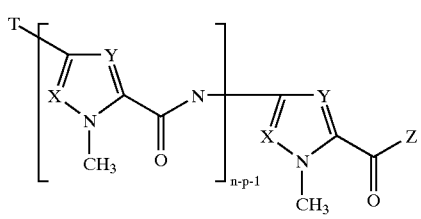

wherein n, p, X, Y, T and Z are as defined above, by reaction with a compound of formula:

(VIII)

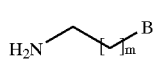

wherein m is as defined above and B is selected from:

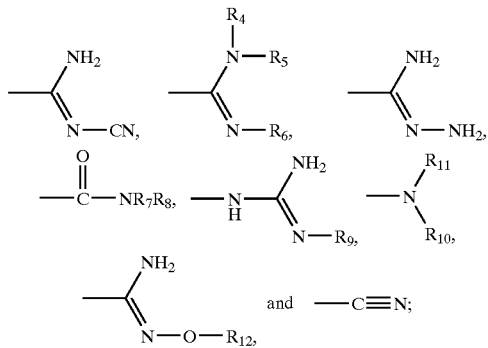

wherein $R_4$, $R_5$, $R_6$, $R_7$, $R_8$, $R_9$, $R_{10}$, $R_{11}$ and $R_{12}$ are as defined above.

Finally, the compounds of formula (V) wherein B is other than

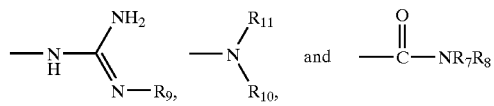

can be prepared through the so-called Pinner reaction, by reacting a compound of formula (V) wherein B is equal to CN with a suitable amino compound as set forth above under points (i), (ii), (iii) or (iv).

Also the compounds of formula (III) are known or easily prepared according to conventional methods.

See, for a general reference, WO96/05196; J.C.S. 1947-1032 and JACS 62, 3495 (1940).

The reaction of process (b) is carried out according to the method reported in WO 97/43258.

The compounds of formula (IV), (VI), (VII) and (VIII) are known compounds, or may be obtained by known methods (see, for a general reference, Tetrahedron, 34, 2389–2391, 1978; J. Org. Chem., 46, 3492–3497, 1981; J. Org. Chem., 52, 3493–3501, 1987; WO96/05196 and WO97/43258.

The optional conversion of a compound of formula (I) into a pharmaceutically acceptable salt, as well as the preparation of a free compound starting from a salt, may be carried out by known standard methods.

Well known procedures such as, e.g., fractional crystallization or chromatography, may also be followed for separating a mixture of isomers of formula (I) into the single isomers.

The compounds of formula (I) may be purified by conventional techniques such as, e.g., silica gel or alumina column chromatography, and/or by recrystallization from an organic solvent such as, e.g., a lower aliphatic alcohol, e.g. methyl, ethyl or isopropyl alcohol, or dimethylformamide.

The compounds of the invention show cytotoxic properties towards tumor cells so that they can be useful as antineoplastic agents, e.g. to inhibit the growth of various tumors such as, for instance, carcinomas, e.g. mammary carcinoma, lung carcinoma, bladder carcinoma, colon carcinoma, ovary and endometrial tumors. Other neoplasias in which the compounds of the invention could find application are, for instance, sarcomas, e.g. soft tissue and bone sarcomas, and the hematological malignancies such as, e.g., leukemias.

The antitumor activity of the compounds of formula (I) was evaluated in vitro by cytotoxicity studies carried out on murine L1210 leukemia cell. Cells were derived from in vivo tumors and established in cell culture. Cells were used until the tenth passage. Cytotoxicity was determined by counting surviving cells after 4 hours treatment and 48 hours growth in drug-free medium.

The percentage of cell growth in the treated cultures was compared with that of controls. Doses inhibiting 50% of the cellular growth in respect to controls, expressed as $ID_{50}$ values, were calculated on dose-response curves.

The compounds of the invention can be administered by the usual routes, for example, parenterally, e.g. by intravenous injection or infusion, intramuscularly, subcutaneously, topically or orally.

The dosage depends on the age, weight and conditions of the patient and on the administration route.

For example, a suitable dosage for administration to adult humans may range from about 0.05 to about 100 mg pro dose 1–4 times a day.

The pharmaceutical compositions of the invention contain a compound of formula (I) as the active substance, in association with one or more pharmaceutically acceptable excipients.

The pharmaceutical compositions of the invention are usually prepared following conventional methods and are administered in a pharmaceutically suitable form.

For instance, solutions for intravenous injection or infusion may contain sterile water as a carrier or, preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

In the form for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl-cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

Furthermore, according to the present invention, there is provided a method of treating tumors in a patient in need of it, comprising administering to the said patient a composition of the invention.

The following examples illustrate but do not limit the invention.

The abbreviations DMF and DMSO-$d_6$ stand for dimethylformamide and deutero-dimethylsulfoxide, respectively.

EXAMPLE 1

3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propioncyanamadine Step I: The Intermediate 1-methyl-3-(α-bromoacrylamido)pyrazole-5-carboxylic Acid.

To a solution containing 0.620 g of ethyl 3-aminopyrazole-1-methyl-5-carboxylate and 0.3 g of 2-bromoacrylic acid in 10 ml of dioxane, 0.412 g of N-N'dicyclohexylcarbodiimide were added and the mixture was stirred at room temperature overnight. After filtration, the solvent was evaporated in vacuo, the solid residue was dissolved in 50 ml of ethyle acetate, treated with a saturated solution of sodium bicarbonate and then with 10% hydrochloric acid. The organic phase was dried over anhydrous sodium sulfate and the solvent evaporated in vacuo. The solid residue was purified by recrystallization from ethanol-water to yield 0.48 g of ethyl 1-methyl-3-(α-bromoacrylamido)-pyrazole-5-carboxylate. The derivative (0.48 g) was dissolved in 10 ml of dioxane and added of 1.6 ml of 2 N potassium hydroxide. The mixture was stirred overnight, acidified with 10% hydrochloric acid and the solvent was evaporated in vacuo yielding 0.40 g of intermediate.

PMR(DMSO-$d_6$) d: 12.9 (b.s., 1H), 10.1 (s, 1H), 7.22 (s, 1H), 6.95 (d, J=3.7 Hz, 1H), 6.43 (d, J=3.7 Hz, 1H), 4.02 (s, 3H).

By analogous procedure the following compounds can be prepared:

1-methyl-4-(α-bromoacrylamido)pyrrole-2-carboxylic acid

PMR (DMSO-$d_6$) d: 12.2 (b.s., 1H), 10.2 (s, 1H), 7.38 (d, J=1.8 Hz, 1H), 6.85 (d, J=1.8 Hz, 1H), 6.68 (d, J=3.7 Hz, 1H), 6.2 (d, J=3.7 Hz, 1H), 3.82 (s, 3H);

1-methyl-4-(α-bromoacrylamido)imidazole-2-carboxylic acid

PMR (DMSO-$d_6$) d: 11.08 (s, 1H), 7.58 (s, 1H), 6.82 (d, J=2.3 Hz, 1H), 6.29 (d, J=2.3.8 Hz, 1H), 3.81 (s, 3H);

1-methyl-3-(α-chloroacrylamido)pyrazole-5-carboxylic acid;

1-methyl-2-(α-chloroacrylamido)pyrrole-4-carboxylic acid

FAB-MS: m/z 228 (40, [M+H]$^+$), 193, 139

PMR(DMSO-$d_6$) d: 12.20 (b.s., 1H), 10.24 (s, 1H), 7.39 (d, J=2.0 Hz, 1H), 6.88 (d, J=2.0 Hz, 1H), 6.37 (d, J=2.2 Hz, 1H), 5.99 (d, J=2.2 Hz, 1H), 3.81 (s, 3H);

1-methyl-4-(α-chloroacrylamido)imidazole-2-carboxylic acid.

Step II: The Intermediate 1-methyl-3-(α-bromoacrylamido)pyrazole 5-carboxyl Chlodride The intermediate obtained from step I (1.2 g) was dissolved in 40 ml of benzene and added of 10 ml of SOCl$_2$. After refluxing for 1 hour the solution was evaporated to dryness in vacuo to give 1.4 g of the intermediate.

By analogous procedure and by using the opportune starting materials the following compounds can be obtained:

1-methyl-4-(α-bromoacrylamido)pyrrole-2-carboxyl chloride;

1-methyl-4-(α-bromoacrylamido)imidazole-2-carboxyl chloride;

1-methyl-3-(α-chloroacrylamido)pyrazole-5-carboxyl chloride;

1-methyl-4-(α-chloroacrylamido)pyrrole-2-carboxyl chloride;

1-methyl-4-(α-chloroacrylamido)imidazole-2-carboxyl chloride.

Step III: The Intermediate 3-[1-methyl-4-[1-methyl-4-(1-methyl-4-aminopyrrole-2-carboxamido]pyrrole-2-carboxamido]pyrrole-2-carboxamido)propioncyanamidine hydrochloride To a solution of 324 mg of cyanamide in 20 ml of DMF 186 mg of sodium hydride were added. The mixture was stirred at room temperature for 30 min. and then added to a solution of 1 g of distamycin A in 10 ml DMF. The solution was stirred at room temperature for two hours and acetic acid was then added up to pH=7. The solvent was removed at reduced pressure and the crude residue purified by flash chromatography (methylene chloride/methanol: 9/1) to give 900 mg of 3-[1-methyl-4-(1-methyl-4-[1-methyl-4-formamidopyrrole-2-carboxamido]pyrrole-2-carboxamido]pyrrole-2-carboxamido]propioncyanamidine which was dissolved in 50 ml of methanol and added with 5 ml of 2 N hydrochloric acid.

The reaction mixture was stirred at room temperature for two days, the solvent was evaporated in vacuo and the solid residue suspended in 200 ml of ethyl acetate, yielding after filtration 600 mg of the intermediate.

FAB-MS: m/z 479 (65, [M+H]$^+$);

PMR (DMSO-$d_6$) δ: 10.11 (s, 3H), 9.97 (s, 1H), 9.80–9.60 (b.s., 2H), 8.50–8.00 (b.s., 3H), 7.40 (t, J=5.8 Hz, 1H), 7.25 (d, J=1.7 Hz, 1H), 7.19 (d, J=1.7 Hz, 1H), 7.08 (d, J=1.7 Hz, 1H), 7.06 (d, J=1.7 Hz, 1H), 6.94 (d, J=1.7 Hz, 1H), 6.88 (d, J=1.7 Hz, 1H), 3.81 (s, 3H), 3.79 (s, 3H), 3.75 (s, 3H), 3.41 (m, 2H), 2.70 (m, 2H).

By analogous procedure and by using the opportune starting materials the following compounds can be obtained:

3-[1-methyl-4-[1-methyl-4-[1-methyl-4-aminoimidazole-2-carboxamido]pyrrole-2-carboxamido]pyrrole-2-carboxamido]propioncyanamidine hydrochloride;

3-[1-methyl-4-[1-methyl-4-[1-methyl-3-aminopyrazole-5-carboxamido]pyrrole-2-carboxamido]pyrrole-2-carboxamido]propioncyanamidine hydrochloride.

Step IV: The Title Compound

To a solution of 205 mg of the intermediate obtained from step III, 100 mg of NaHCO$_3$ in 40 ml of water and 20 ml of dioxane, a solution of 175 mg of the intermediate obtained from step II in 40 ml of dioxane was added. The solution was stirred for 2 hours at room temperature then the solvent was evaporated in vacuo and the crude residue was purified by flash chromatography (methylene chloride/methanol: 10/1) to give 145 mg of the title compound as a white solid.

FAB-MS: m/z 734 (90, [M+H]$^+$);

PMR (DMSO-d$_6$) δ: 11.00 (s, 1H), 10.47 (s, 1H), 9.99 (s, 1H), 9.90 (s, 1H), 8.80–8.00 (b.s., 3H), 7.35 (s, 1H), 7.30 (d, J=1.7 Hz, 1H), 7.24 (d, J=1.7 Hz, 1H), 7.19 (d, J=1.7 Hz, 1H), 7.08 (d, J=1.7 Hz, 1H), 7.03 (d, J=1.7 Hz, 1H), 6.87 (d, J=1.7 Hz, 1H), 6.79 (d, J=3.1 Hz, 1H), 6.31 (d, J=3.1 Hz, 1H), 4.04 (s, 3H), 3.86 (s, 3H), 3.83 (s, 3H), 3.79 (s, 3H), 3.40 (b.s., 2H), 2.80–2.30 (b.s., 2H).

By analogous procedure and by using the opportune starting materials the following compounds can be obtained:

(18) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propioncyanamidine FAB-MS: m/z 734 (95, [M+H]$^+$);

PMR (DMSO-d$_6$) δ: 10.52 (s, 1H), 10.12 (s, 1H), 9.94 (s, 1H), 9.90 (s, 1H), 8.80–8.00 (b.s., 3H), 7.52 (s, 1H), 7.26 (d, J=1.7 Hz, 1H), 7.23 (d, J=1.7 Hz, 1H), 7.18 (d, J=1.7 Hz, 1H), 7.14 (d, J=1.7 Hz, 1H), 7.04 (d, J=1.7 Hz, 1H), 6.87 (d, J=1.7 Hz, 1H), 6.80 (d, J=3.0 Hz, 1H), 6.30 (d, J=3.0 Hz, 1H), 3.97 (s, 3H), 3.84 (s, 3H), 3.83 (s, 3H), 3.79 (s, 3H), 3.60–3.20 (b.s., 2H), 2.80–2.30 (b.s., 2H);

(41) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propioncyanamidine;

(59) 3-(1-methyl-4-(1-methyl-4-(1-methyl-3-(α-bromoacrylamido)pyrazole-5-carboxamido)pyrrole-2-carboxamido)pyrrole-2-carboxamido)propioncyanamidine;

(70) 3-(1-methyl-4-(1-methyl-4-(1-methyl-4-(α-bromoacrylamido)imidazole-2-carboxamido)pyrrole-2-carboxamido)pyrrole-2-carboxamido)propioncianamidine.

EXAMPLE 2

3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N-methylamidine hydrochloride Step I: The Intermediate 3-[1-methyl-4-[1-methyl-4-[1-methyl-4-aminopyrrole-2-carboxamido]pyrrole-2-carboxamido]pyrrole-2-carboxamido]propion-N-methylamidine dihydrochloride A solution of 2 g of distamycin A in 50 ml DMF was treated with 0.38 ml of methylamine hydrochloride 80%. After 8 hours additional 0.25 equivalents of methylanine hydrochloride 80% were added. The solution was evaporated to dryness and the crude residue was purified by flash chromatography (methylene chloride/methanol: 8/2) to give 1.5 g of 3-[1-methyl-4-[1-methyl-4-[1-methyl-4-formidopyrrole-2-carboxamido]pyrrole-2-carboxamido]pyrrole-2-carboxamido]propion-N-methylamidine hydrochloride which was dissolved in 40 ml of methanol and added with 5 ml of 2 N hydrochloric acid.

The reaction was stirred at room temperature for two days, the solvent evaporated in vacuo and the solid residue suspended in 200 ml of ethyl acetate, yielding after filtration 1.4 g of the intermediate.

FAB-MS: m/z 468 (40, [M+H]$^+$);

PMR (DMSO-d$_6$) δ: 10.20 (s, 3H), 10.18 (s, 1H), 9.98 (s, 1H), 9.65 (m, 1H), 9.20 (s, 1H), 8.63 (s, 1H), 8.25 (t, J=5.8 Hz, 1H), 7.25 (d, J=1.7 Hz, 1H), 7.19 (d, J=1.7 Hz, 1H), 7.11 (d, J=1.7 Hz, 1H), 7.08 (d, J=1.7 Hz, 1H), 7.05 (d, J=1.7 Hz, 1H), 6.91 (d, J=1.7 Hz, 1H), 3.90 (s, 3H), 3.85 (s, 3H), 3.79 (s, 3H), 3.60–3.40 (m, 2H), 2.80 (d, J=6 Hz, 3H), 2.61 (m, 2H).

By analogous procedure and by using the opportune starting materials the following compounds can be obtained:

3-[1-methyl-4-[1-methyl-4-[1-methyl-3-aminopyrazole-5-carboxamido]pyrrole-2-carboxamido]pyrrole-2-carboxamido]propion-N-methylamidine dihydrochloride;

3-(1-methyl-4-[1-methyl-4-[1-methyl-4-aminoimidazole-2-carboxamido)pyrrole-2-carboxamido]pyrrole-2-carboxamido]propion-N-methylamidine dihydrochloride;

3-[1-methyl-5-[1-methyl-4-[1-methyl-4-aminopyrrole-2-carboxamidolpyrrole-2-carboxamido]pyrazole-3-carboxamido]propion-N-methylamidine dihydrochloride;

3-[1-methyl-4-[1-methyl-4-[1-methyl-4-aminopyrrole-2-carboxamido]pyrrole-2-carboxamido]imidazole-2-carboxamido]propion-N-methylamidine dihydrochloride.

Step II: The Title Compound

To a solution containing 0.20 g of the intermediate obtained from step I in 10 ml of dry DMF, 0.15 g of intermediate obtained from example I step I, 0.153 g of 1-ethyl-3-(3'-dimethylaminopropyl)carbodiimide hydrochloride and 0.09 ml of N,N'-diisopropylethylamine were added. The mixture was stirred overnight at room temperature and brought to pH 4–5 with 10% hydrochloric acid.

After evaporation in vacuo of the solvent a solid residue was obtained which was purified by flash chromatography (methylene chloride/methanol: 8/2) yielding 0.13 g of the title compound.

FAB-MS: m/z 723 (95, [M+H]$^+$);

PMR (DMSO-d$_6$) δ: 11.02 (s, 1H), 10.48 (s, 1H), 10.00 (s, 1H), 9.92 (s, 1H), 9.52 (q, J=5.0 Hz, 1H), 9.12 (b.s., 1H), 8.56 (b.s., 1H), 8.22 (t, J=5.0 Hz, 1H), 7.35 (s, 1H), 7.31 (d, J=1.7 Hz, 1H), 7.24 (d, J=1.7 Hz, 1H), 7.18 (d, J=1.7 Hz, 1H), 7.09 (d, J=1.7 Hz, 1H), 7.06 (d, J=1.7 Hz, 1H), 6.93 (d, J=1.7 Hz, 1H), 6.80 (d, J=3.2 Hz, 1H), 6.31 (d, J=3.2 Hz, 1H), 4.00 (s, 3H), 3.86 (s, 3H), 3.83 (s, 3H), 3.79 (s, 3H), 3.49 (m, 2H), 2.78 (d, J=5.0 Hz, 3H), 2.59 (m, 2H).

By analogous procedure and by using the opportune starting materials the following compounds can be obtained:

(3) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-N-methylamidine;

(19) 3-(1-methyl-4-(1-methyl-4-(1-methyl-4-(1-methyl-4-(α-bromoacrylamido)imidazole-5-carboxamido)pyrrole-2-carboxamido)pyrrole-2-carboxamido)pyrrole-2-carboxamido)propion-N-methylamidine FAB-MS: m/z 723 (100, [M+H]$^+$);

PMR (DMSO-d$_6$) δ: 10.54 (s, 1H), 10.11 (s, 1H), 9.97 (s, 1H), 9.91 (s, 1H), 9.50 (b.s., 1H), 9.10 (b.s., 1H), 8.55 (b.s., 1H), 8.21 (t, J=5.6 Hz, 1H), 7.52 (s, 1H), 7.26 (d, J=1.7 Hz, 1H), 7.23 (d, J=1.7 Hz, 1H), 7.17 (d, J=1.7 Hz, 1H), 7.16 (d; J=1.7 Hz, 1H), 7.06 (d, J=1.7 Hz, 1H), 6.92 (d, J=1.7 Hz, 1H), 6.80 (d, J=3.0 Hz, 1H), 6.30 (d, J=3.0 Hz, 1H), 3.97 (s, 3H), 3.84 (s, 3H), 3.83 (s, 3H), 3.79 (s, 3H), 3.49 (m, 2H), 2.78 (d, J=4.7 Hz, 3H), 2.58 (t, J=6.0 Hz, 2H);

(32) 3-(1-methyl-4-(1-methyl-4-(1-methyl-3-(1-methyl-3-(α-bromoacrylamido)pyrazole-5-carboxamido)pyrrole-5-carboxamido)pyrrole-2-carboxamido)pyrrole-2-carboxamido)propion-N-methylamidine;

(33) 3-(1-methyl-4-(1-methyl-4-(1-methyl-3-(1-methyl-3-(α-chloroacrylamido)pyrazole-5-carboxamido)pyrazole-5-carboxamido)pyrrole-2-carboxamido)pyrrole-2-carboxamido)propion-N-methylamidine;

(46) 3-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propion-N-methylamidine;

(50) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)imidazole-2-carboxamido)propion-N-methylamidine;

(54) 3-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)propion-N-methylamidine;

(60) 3-(1-methyl-4-(1-methyl-4-(1-methyl-3-(α-bromoacrylamido)pyrazole-5-carboxamido)pyrrole-2-carboxamido)pyrrole-2-carboxamido)propion-N-methylamidine;

(61) 3-(1-methyl-4-(1-methyl-4-(1-methyl-3-(α-chloroacrylamido)pyrazole-5-carboxamido)pyrrole-2-carboxamido)pyrrole-2-carboxamido)propion-N-methylamidine;

(71) 3-(1-methyl-4-(1-methyl-4-(1-methyl-4-(α-bromoacrylamido)imidazole-2-carboxamido)pyrrole-2-carboxamido)pyrrole-2-carboxamido)propion-N-methylamidine.

EXAMPLE 3

3-(1-methyl-4-(1-mothyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N,N'-dimethylamidine hydrochloride Step I: The Intermediate 3-[1-methyl-4-[1-methyl-4-[1-methyl-4-aminopyrrole-2-carboxamido]pyrrole-2-carboxamido]pyrrole-2-carboxamido]propion-N,N'-dimethylamidine dihydrochloride A solution of 1.5 g of distamycin A in 40 ml DMF was heated to 80° C. and treated with 4 ml of methylamine hydrochloride 80%. After 4 hours additional 5 equivalents (4 ml) of methylamine hydrochloride 80% were added. The solution was evaporated to dryness and the crude residue was purified by flash chromatography (methylene chloride/methanol:8/2) to yield 1.2 g of 3-[1-methyl-4-[1-methyl-4-[1-methyl-4-formamidopyrrole-2-carboxamido]pyrrole-2-carboxamido]pyrrole-2-carboxamido]propion-N,N'-dimethyl-amidine hydrochloride which was dissolved in 40 ml of methanol and added with 5 ml of 2 N hydrochloric acid solution.

The reaction was stirred at room temperature for two days, the solvent evaporated in vacuo and the solid residue suspended in 200 ml of ethyl acetate, yielding after filtration 1.4 g of the intermediate.

FAB-MS: m/z 482 (45, [M+H]$^+$);

PMR (DMSO-d$_6$) δ: 10.21 (s, 3H), 10.18 (s, 1H), 9.98 (s, 1H), 9.61 (m, 1H), 8.85 (s, 1H), 8.39 (t, J=5.8 Hz, 1H), 8.00–7.70 (b.s., 1H), 7.28 (d, J=1.7 Hz, 1H), 7.22 (d, J=1.7 Hz, 1H), 7.12 (d, J=1.7 Hz, 1H), 7.08 (d, J=1.7 Hz, 1H), 7.03 (d, J=1.7 Hz, 1H), 6.92 (d, J=1.7 Hz, 1H), 3.92 (s, 3H), 3.89 (s, 3H), 3.86 (s, 3H), 3.60–3.40 (m, 2H), 3.02 (d, J=6 Hz, 3H), 2.80 (d, J=6 Hz, 3H), 2.72 (m, 2H).

By analogous procedure and by using the opportune starting material the following compounds can be obtained:

3-[1-methyl-4-[1-methyl-4-[1-methyl-3-aminopyrazole-5-carboxamido]pyrrole-2-carboxamido]pyrrole-2-carboxamido]propion-N,N'-dimethylamidine dihydrochloride;

3-[1-methyl-4-[1-methyl-4-[1-methyl-4-aminoimidazole-2-carboxamido]pyrrole-2-carboxamido]pyrrole-2-carboxamido]propion-N,N'-dimethylamidine dihydrochloride;

3-[1-methyl-3-[1-methyl-4-[1-methyl-4-aminopyrrole-2-carboxamido]pyrrole-2-carboxamido]pyrazole-5-carboxamido]propion-N,N'-dimethylamidine dihydrochloride;

3-[1-methyl-4-[1-methyl-4-[1-methyl-4-aminopyrrole-2-carboxamido]pyrrole-2-carboxamido]imidazole-2-carboxamido]propion-N,N'-dimethylamidine dihydrochloride;

3-[1-methyl-4-[1-methyl-4-[1-methyl-4-aminopyrrole-2-carboxamido]pyrrole-2-carboxamidolpyrrole-2-carboxamido]propion-N,N,N'-trimethylamidine dihydrochloride FAB-MS: m/z 482, (45, [M+H]$^+$);

PMR (DMSO-d$_6$) δ: 10.21 (s, 3H), 10.18 (s, 1H), 9.61 (m, 1H), 8.85 (s, 1H), 8.39 (t, J=5.8 Hz, 1H), 8.00–7.70 (b.s., 1H), 7.28 (d, J=1.7 Hz, 1H), 7.22 (d, J=1.7 Hz, 1H), 7.12 (d, J=1.7 Hz, 1H), 7.08 (d, J=1.7 Hz, 1H), 7.03 (d, J=1.7 Hz, 1H), 6.92 (d, J=1.7 Hz, 1H), 3.92 (s, 3H), 3.89 (s, 3H), 3.86 (s, 3H), 3.60–3.40 (m, 2H), 3.02 (d, J=6 Hz, 3H), 2.80 (d, J=6 Hz, 3H), 2.72 (m, 2H);

3-[1-methyl-4-[1-methyl-4-[1-methyl-3-aminopyrazole-5-carboxamido]pyrrole-2-carboxamido]pyrrole-2-carboxamido]propion-N,N,N'-trimethylamidine dihydrochloride;

3-[1-methyl-4-[1-methyl-4-[1-methyl-4-aminoimidazole-2-carboxamido]pyrrole-2-carboxamido]pyrrole-2-carboxamido]propion-N,N,N'-trimethylamidine dihydrochloride.

Step II: The Title Compound

To a solution of 100 mg of the intermediate obtained from step I, 50 mg of NaHCO$_3$ in 10 ml of water, was added to a solution of 85 mg of the intermediate obtained from step II example 1 in 15 ml of benzene. The slurry was vigorously stirred for 1 hour at room temperature then the solvent was evaporated in vacuo and the crude residue was purified by flash chromatography (methylene chloride/methanol: 8/2) to give 80 mg of the title compound as a white solid.

FAB-MS: m/z 737 (95, [M+H]$^+$);

PMR (DMSO-d$_6$) δ: 11.02 (s, 1H), 10.47 (s, 1H), 9.99 (s, 1H), 9.92 (s, 1H), 9.40 (q, J=4.7 Hz, 1H), 8.65 (q, J=4.7 Hz, 1H), 8.27 (t, J=5.0 Hz, 1H), 7.34 (s, 1H), 7.30 (d, J=1.7 Hz, 1H), 7.23 (d, J=1.7 Hz, 1H), 7.18 (d, J=1.7 Hz, 1H), 7.08 (d, J=1.7 Hz, 1H), 7.06 (d, J=1.7 Hz, 1H), 6.93 (d, J=1.7 Hz, 1H), 6.79 (d, J=3.0 Hz, 1H), 6.32 (d, J=3.0 Hz, 1H), 4.04 (s, 3H), 3.86 (s, 3H), 3.83 (s, 3H), 3.79 (s, 3H), 3.45 (m, 2H), 3.00 (d, J=4.7 Hz, 3H), 2.77 (d, J=4.7 Hz, 3H), 2.70 (t, J=6.6 Hz, 2H).

By analogous procedure and by using the opportune starting materials the following compounds can be obtained:

(20) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N,N'-dimethylamidine FAB-MS: m/z 737 (90, [M+H]$^+$);

PMR (DMSO-d$_6$) δ: 11.54 (s, 1H), 10.12 (s, 1H), 9.96 (s, 1H), 9.92 (s, 1H), 9.43 (q, J=5.0 Hz, 1H), 8.68 (q, J=4.7 Hz, 1H), 8.28 (t, J=4.9 Hz, 1H), 7.52 (s, 1H), 7.26 (d, J=1.7 Hz, 1H), 7.23 (d, J=1.7 Hz, 1H), 7.18 (d, J=1.7 Hz, 1H), 7.15 (d,

J=1.7 Hz, 1H), 7.06 (d, J=1.7 Hz, 1H), 6.92 (d, J=1.7 Hz, 1H), 6.80 (d, J=3.0 Hz, 1H), 6.30 (d, J=3.0 Hz, 1H), 3.97 (s, 3H), 3.84 (s, 3H), 3.83 (s, 3H), 3.79 (s, 3H), 3.40 (m, 2H), 3.00 (d, J=4.7 Hz, 3H), 2.77 (d, J=5.0 Hz, 3H), 2.71 (t, J=6.8 Hz, 2H);

(5) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-N,N'-dimethylamidine;

(34) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N,N'-dimethylamidine;

(47) 3-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propion-N,N'-dimethylamidine;

(55) 3-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)propion-N,N'-dimethylamidine;

(62) 3-(1-methyl-4-(1-methyl-4-(1-methyl-3-(α-bromoacrylamido)pyrazole-5-carboxamido)pyrrole-2-carboxamido)pyrrole-2-carboxamido)propion-N,N'-dimethylamidine;

(72) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N'-dimethylamidine;

(6) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N,N,N'-trimethylamidine;

(21) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N,N,N'-trimethylamidine;

(35) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N,N,N'-trimethylamidine;

(63) 3-(1-methyl-4-(1-methyl-4-(1-methyl-3-(α-bromoacrylamido)pyrazole-5-carboxamido)pyrrole-2-carboxamido)pyrrole-2-carboxamido)propion-N,N,N'-trimethylamidine;

(73) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N,N'-trimethylamidine.

EXAMPLE 4

2-(1-methyl-4-(1-methyl-4-(1-methyl-4-(1-methyl-3-(α-bromoacrylamido)pyrazole-5-carboxamido)pyrrole-2-carboxamido)pyrrole-2-carbo amido)pyrrole-2-carboxamido)ethylguanidine hydrochloride Step I: The Intermediate 2-aminoethylguanidine dihydrochloride A solution of commercial N-BOC-ethylendiamine (1 g) in dry ethanol (100 ml) and 2-methyl-2-thiopseudourea hydroiodide (1.5 g) was refluxed for 8 hours. The solvent was removed at reduced pressure and the crude residue purified by flash chromatography (methylene chloride/methanol: 9/1) to yield 1.5 g of N-BOC-2-aminoethylguanidine hydroiodide as a yellow oil which was dissolved in methanolic hydrochloric acid solution 5N (20 ml) and stirred at room temperature for 3 hours. The white precipitate was collected, washed with dry ethanol, affording 700 mg of the intermediate.

FAB-MS: m/z 103 (20, [M+H]$^+$);

PMR (DMSO-d$_6$) δ: 8.38 (b.s., 3H), 7.97 (t, J=6 Hz, 1H), 7.51 (b.s., 4H), 3.45 (m, 2H), 2.92 (m, 2H).

Step II: The Intermediate 2-[1-methyl-4[1-methyl-4[1-methyl-4-aminopyrrole-2-carboxamido]pyrrole-2-carboxamido]pyrrole-2-carboxamido]ethylguanidine dihydrochloride A solution of 1-methyl-4-[1-methyl-4-[1-methyl-4-nitropyrrole-2-carboxamido]pyrrole-2-carboxamido]pyrrole-2-carboxylic acid (590 mg) (prepared as reported in Tetrahedron 34, 2389–2391, 1978) in 20 ml of DMF, 2-aminoethylguanidine dihydrochloride (500 mg), 1-hydroxybenzotriazole hydrate (350 mg), dicycloexylcarbodiimide (880 mg), and sodium bicarbonate (385 mg) was stirred at 70° C. for 4 hours. The solution obtained after filtration was evaporated in vacuo and the residue purified by flash chromatography (methylene chloride/methanol: 8/2) to yield 800 mg of 2-[1-methyl-4-[1-methyl-4-[1-methyl-4-nitropyrrole-2-carboxamido]pyrrole-2-carboxamido]pyrrole-2-carboxamido]ethylguanidine hydrochloride, which was dissolved in methanol (100 ml), treated with 1N hydrochloric acid solution (2 ml) and reduced over Pd catalyst (10% on charcoal) under hydrogen atmosphere (50 psi) into a Parr apparatus. The solution obtained after filtration of the catalyst was evaporated in vacuo and the solid residue washed with dry ethanol to yield 750 mg of the intermediate as a brown powder.

FAB-MS: m/z 469 (15, [M+H]$^+$);

PMR (DMSO-d$_6$) δ: 10.38–10.11 (b.s., 4H), 9.98 (s, 1H), 8.28 (b.s., 1H), 8.19 (d, J=1.7 Hz, 1H), 7.73, (b.s., 1H), 7.63 (d, J=1.7 Hz, 1H), 7.60–7.00 (b.s., 4H), 7.28 (d, J=1.7 Hz, 1H), 7.20 (d, J=1.7 Hz, 1H), 7.1 (d, J=1.7 Hz, 1H), 6.92 (d, J=1.7 Hz, 1H), 3.93 (s, 3H), 3.90 (s, 3H), 3.82 (s, 3H), 3.28 (m, 4H).

By analogous procedure and by using the suitable starting materials the following compounds can be obtained:

3-[1-methyl-4-[1-methyl-4-(1-methyl-4-aminopyrrole-2-carboxamido)pyrrole-2-carboxamido]pyrrole-2-carboxamido]propioncyanamidine hydrochloride;

3-[1-methyl-4-[1-methyl-4-[1-methyl-4-aminoimidazole-2-carboxamido]pyrrole-2-carboxamido]pyrrole-2-carboxamido]propioncyanamidine hydrochloride;

3-[1-methyl-4-[1-methyl-4-[1-methyl-4-aminopyrrole-2-carboxamido]pyrrole-2-carboxamido]pyrrole-2-carboxamido]propion-N-methylamidine dihydrochloride;

3-[1-methyl-4-[1-methyl-4-[1-methyl-3-aminopyrazole-5-carboxamido]pyrrole-2-carboxamido]pyrrole-2-carboxamido]propion-N-methylamidine dihydrochloride;

3-[1-methyl-4-[1-methyl-4-(1-methyl-4-aminopyrrole-2-carboxamido]pyrrole-2-carboxamido]pyrrole-2-carboxamido]propion-N,N'-dimethylamidine dihydrochloride;

3-[1-methyl-3-[1-methyl-4-[1-methyl-4-aminopyrrole-2-carboxamidolpyrrole-2-carboxamido]pyrazole-5-carboxamido]propion-N,N'-dimethylamidine dihydrochloride;

3-[1-methyl-4[1-methyl-4[1-methyl-4-aminopyrrole-2-carboxamido]pyrrole-2-carboxamido]pyrrole-2-carboxamido]propionamide hydrochloride;

3-[1-methyl-4[1-methyl-4[1-methyl-4-aminopyrrole-2-carboxamido]pyrrole-2-carboxamido]imidazole-2-carboxamido]propionamide hydrochloride;

3-[1-methyl-4-[1-methyl-4-(1-methyl-4-aminopyrrole-2-carboxamido]pyrrole-2-carboxamido]pyrrole-2-carboxamido]propion-N,N-dimethylamine dihydrochloride;

3-[1-methyl-4-[1-methyl-4-[1-methyl-4-aminoimidazole-2-carboxamido]pyrrole-2-carboxamido]pyrrole-2-carboxamido]propion-N,N-dimethylamine dihydrochloride;

3-[1-methyl-4[1-methyl-4[1-methyl-4-aminopyrrole-2-carboxamido]pyrrole-2-carboxamido]pyrrole-2-carboxamido]propionitrile hydrochloride;

2-[1-methyl-[1-methyl-4-aminopyrrole-2-carboxamido]pyrrole-2-carboxamido]ethylguanidine dihydrochloride;

2-[1-methyl-[1-methyl-3-aminopyrazole-5-carboxamido]pyrrole-2-carboxamido]ethylguanidine dihydrochloride;

2-[1-methyl-[1-methyl-4-aminoimidazole-2-carboxamido]pyrrole-2-carboxamido]ethylguanidinedihydrochloride;

2-[1-methyl-3[1-methyl-4[1-methyl-4-aminopyrrole-2-carboxamidolpyrrole-2-carboxamido]pyrazole-5-carboxamido]ethylguanidine hydrochloride;

2-[1-methyl-4[1-methyl-4[1-methyl-4-aminopyrrole-2-carboxamido]pyrrole-2-carboxamido]imidazole-2-carboxamido]ethylguanidine hydrochloride.

Step III: The Title Compound

A solution of 250 mg of 1-methyl-3-(α-bromoacrylamido)pyrrole-5-carboxyl chloride (prepared as reported in Example 1 step III) in 15 ml of benzene, was added to a solution of the intermediate obtained from step II (250 mg) and 82 mg of $NaHCO_3$ in 5 ml of $H_2O$. The solution was vigorously stirred for 8 hours at room temperature, then evaporated in vacuo and the crude residue was purified by flash chromatography (methylene chloride/methanol: 8/2) to yield 220 mg of the title compound as a yellow solid.

FAB-MS: m/z, 723 (45, [M+H]$^+$);

PMR (DMSO-$d_6$) δ: 10.30 (s, 1H), 9.95 (s, 1H), 9.92 (s, 1H), 9.90 (s, 1H), 8.10 (t, J=5.9 Hz, 1H), 7.56 (t, J=5.9, 1H), 7.34 (s, 1H) 7.2 (b.s., 4H), 7.23 (m, 3H), 7.19 (d, J=1.7 Hz, 1H), 7.04 (d, J=1.7 Hz, 1H), 6.98 (d, J=1.7 Hz, 1H), 6.68 (d, J=2.9 Hz, 1H), 6.21 (d, J=2.9 Hz, 1H), 3.85 (s, 3H), 3.84 (s, 3H), 3.83 (s, 3H), 3.80 (s, 3H), 3.30 (b.s., 4H).

By analogous procedure and by using the opportune starting materials the following compounds can be obtained:

(10) 2-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)ethylguanidine;

(24) 2-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)ethylguanidine;

(25) 2-(1-methyl-4-(1-methyl-4-(1-methyl-4-(1-methyl-4-(α-chloroacrylamido)imidazole-2-carboxamido)pyrrole-2-carboxamido)pyrrole-2-carboxamido)pyrrole-2-carboxamido)ethylguanidine;

(37) 2-(1-methyl-4-(1-methyl-4-(1-methyl-3-(1-methyl-3-(α-bromoacrylamido)pyrazole-5-carboxamido)pyrrole-2-carboxamido)pyrrole-2-carboxamido)ethylguanidine;

(38) 2-(1-methyl-4-(1-methyl-4-(1-methyl-3-(1-methyl-3-(α-chloroacrylamido)pyrazole-5-carboxamido)pyrazole-5-carboxamido)pyrrole-2-carboxamido)pyrrole-2-carboxamido)ethylguanidine;

(48) 2-(1-methyl-3-(1-methyl-4-(1-methyl-4-(1-methyl-4-(α-bromoacrylamido)pyrrole-5-carboxamido)pyrrole-2-carboxamido)pyrrole-2-carboxamido)pyrazole-5-carboxamido)ethylguanidine;

(52) 2-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)imidazole-2-carboxamido)ethylguanidine;

(56) 2-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)ethylguanidine;

(65) 2-(1-methyl-4-(1-methyl-4-(1-methyl-3-(α-bromoacrylamido)pyrazole-5-carboxamido)pyrrole-2-carboxamido)pyrrole-2-carboxamido)ethylguanidine;

(66) 2-(1-methyl-4-(1-methyl-4-(1-methyl-3-(α-chloroacrylamido)pyrazole-5-carboxamido)pyrrole-2-carboxamido)pyrrole-2-carboxamido)ethylguanidine;

(76) 2-(1-methyl-4-(1-methyl-4-(1-methyl-4-(α-bromoacrylamido)imidazole-2-carboxamido)pyrrole-2-carboxamido)pyrrole-2-carboxamido)ethylguanidine;

(11) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propyl-N,N-dimethylamine;

(26) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propyl-N,N-dimethylamine;

(43) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propion-N,N-dimethylamine;

(77) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N-dimethylamine.

EXAMPLE 5

3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propionamidoxime Step I: The Intermediate 3-[1-methyl-4-1-methyl-4-(1-methyl-4-aminopyrrole-2-carboxamido]pyrrole-2-carboxamido]pyrrole-2-carboxamido)propionamidoxime hydrochloride 1.2 g of 3-[1-methyl-4-[1-methyl-4-[1-metyhyl-4-nitropyrrole-2-carboxamido]pyrrole-2-carboxamido]pyrrole-2-carboxamidol propionitrile (prepared as reported in J.Med.Chem 22,1296–1301,1979) was suspended in dry ethanol and the solution saturated with dry hydrogen chloride. After 24 hours at room temperature, the solvent was evaporated under vacuo and the residue treated with two equivalents of solution of hydroxylamine in dry ethanol. After 24 hours at room temperature, the solvent was evaporated in vacuo and the residue purified by flash chromatography yielding 500 mg of 3-[1-methyl-4-[1-methyl-4-[1-methyl-4-nitropyrrole-2-carboxamido]pyrrole-2-carboxamido]pyrrole-2-carboxamido]propionamidoxime which was dissolved in a mixture of methanol-dioxane-10% hydrochloric acid (4:1:1) and reduced over Pd catalyst (10% on charcoal) under hydrogen atmosphere (50 psi) into a Parr apparatus.

The solution obtained after filtration of the catalyst was evaporated in vacuo, and the solid residue suspended in dry ethanol, and filtered to yield 500 mg of the intermediate.

FAB-MS: m/z 480 (20, (M+H]$^+$);

PMR (DMSO-d$_6$) δ: 10.18 (b.s., 6H), 9.98 (s, 1H), 8.32 (t, J=5.7 Hz, 1H), 7.25 (d, J=1.7 Hz, 1H), 7.20 (d, J=1.7 Hz, 1H), 7.16 (d, J=1.7 Hz, 1H), 7.12 (d, J=1.7 Hz, 1H), 7.10 (d, J=1.7 Hz, 1H), 6.93 (d, J=1.7 Hz, 1H), 3.89 (s, 3H), 3.86 (s, 3H), 3.82 (b.s., 7H), 3.50 (m, 2H), 2.72 (m, 2H).

By analogous procedure and by using the opportune starting materials the following compounds can be obtained:

3-[1-methyl-4-[1-methyl-4-[1-methyl-3-aminopyrazole-5-carboxamido]pyrrole-2-carboxamido]pyrrole-2-carboxamido]propionamidoxime hydrochloride;

3-[1-methyl-4-[1-methyl-4-[1-methyl-4-aminoimidazole-2-carboxamido]pyrrole-2-carboxamido]pyrrole-2-carboxamido]propionamidoxime hydrochloride;

3-[1-methyl-3-[1-methyl-4-[1-methyl-4-aminopyrrole-2-carboxamido]pyrrole-2-carboxamido]pyrazole-5-carboxamido]propionamidoxime hydrochloride;

3-[1-methyl-4-[1-methyl-4-[1-methyl-4-aminopyrrole-2-carboxamido]pyrrole-2-carboxamido]imidazole-2-carboxamido]propionamidoxime hydrochloride;

3-[1-methyl-4-[1-methyl-4-[1-methyl-4-aminopyrrole-2-carboxamido]pyrrole-2-carboxamido]pyrrole-2-carboxamido]propion-N-methylamidoxime hydrochloride;

3-[1-methyl-4-[1-methyl-4-[1-methyl-4-aminopyrrole-2-carboxamido]pyrrole-2-carboxamido]imidazole-2-carboxamido]propion-N-methylamidoxime hydrochloride;

3-[1-methyl-4-[1-methyl-4-[1-methyl-4-aminopyrrole-2-carboxamido]pyrrole-2-carboxamido]pyrrole-2-carboxamido]propion-N-methylamidine dihydrochloride;

3-[1-methyl-4-[1-methyl-4-[1-methyl-4-aminopyrrole-2-carboxamido]pyrrole-2-carboxamido]imidazole-2-carboxamido]propion-N-methylamidine dihydrochloride;

3-[1-methyl-4-[1-methyl-4-[1-methyl-3-aminopyrazole-5-carboxamido]pyrrole-2-carboxamido]pyrrole-2-carboxamido]propion-N-methylamidine dihydrochloride;

3-[1-methyl-4-[1-methyl-4-[1-methyl-4-aminopyrrole-2-carboxamido]pyrrole-2-carboxamido]pyrrole-2-carboxamido]propioncyanamidine hydrochloride;

3-[1-methyl-4-[1-methyl-4-[1-methyl-4-aminoimidazole-2-carboxamido]pyrrole-2-carboxamido]pyrrole-2-carboxamido]propioncyanamidine hydrochloride.

Step II: The Title Compound

To a solution of 200 mg of the intermediate obtained from step I, 100 mg of NaHCO$_3$ in 40 ml of water and 20 ml of dioxane, a solution of 175 mg of the intermediate obtained from step II example I in 40 ml of dioxane was added. The solution was stirred for 2 hours at room temperature then the solvent was evaporated in vacuo and the crude residue was purified by flash chromatography (methylene chloride/methanol: 9/1) to give 120 mg of the title compound as a white solid.

FAB-MS: m/z 724 (50, [M+H]$^+$);

PMR (DMSO-d$_6$) δ: 10.28 (s, 1H), 9.97 (s, 1H), 9.93 (s, 1H), 9.92 (s, 1H), 9.80 (b.s., 2H), 8.32 (m, 1H), 7.35 (s, 1H), 7.25 (d, J=1.7 Hz, 1H), 7.20 (d, J=1.7 Hz, 1H), 7.16 (d, J=1.7 Hz, 1H), 7.12 (d, J=1.7 Hz, 1H), 7.10 (d, J=1.7 Hz, 1H), 6.93 (d, J=1.7 Hz, 1H), 3.89 (s, 3H), 3.86 (s, 3H), 3.82 (b.s., 7H), 3.40 (m, 2H), 2.64 (m, 2H).

By analogous procedure and by using the opportune starting materials the following compounds can be obtained:

(13) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propionamidoxime;

(27) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propionamidoxime;

(28) 3-(1-methyl-4-(1-methyl-4-(1-methyl-4-(1-methyl-4-(α-chloroacrylamido)imidazole-2-carboxamido)pyrrole-2-carboxamido)pyrrole-2-carboxamido)pyrrole-2-carboxamido)propionamidoxime;

(39) 3-(1-methyl-4-(1-methyl-4-(1-methyl-3-(1-methyl-3-(α-bromoacrylamido)pyrazole-5-carboxamido)pyrrole-5-carboxamido)pyrrole-2-carboxamido)pyrrole-2-carboxamido)propionamidoxime;

(49) 3-(1-methyl-3-(1-methyl-4-(1-methyl-4-(1-methyl-4-(α-bromoacrylamido)pyrrole-5-carboxamido)pyrrole-2-carboxamido)pyrrole-2-carboxamido)pyrazole-5-carboxamido)propionamidoxime;

(53) 3-(1-methyl-4-(1-methyl-4-(1-methyl-4-(1-methyl-4-(α-bromoacrylamido)pyrrole-5-carboxamido)pyrrole-2-carboxamido)pyrrole-2-carboxamido)imidazole-2-carboxamido)propionamidoxime;

(57) 3-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)propionamidoxime;

(67) 3-(1-methyl-4-(1-methyl-4-(1-methyl-3-(α-bromoacrylamido)pyrazole-5-carboxamido)pyrrole-2-carboxamido)pyrrole-2-carboxamido)propionamidoxime;

(68) 3-(1-methyl-4-(1-methyl-4-(1-methyl-3-(α-chloroacrylamido)pyrazole-5-carboxamido)pyrrole-2-carboxamido)pyrrole-2-carboxamido)propionamidoxime;

(78) 3-(1-methyl-4-(1-methyl-4-(1-methyl-4-(α-bromoacrylamido)imidazole-2-carboxamido)pyrrole-2-carboxamido)pyrrole-2-carboxamido)propionamidoxime;

(14) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-O-methylamidoxime;

(15) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-O-methylamidoxime;

(29) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-O-methylamidoxime;

(30) 3-(1-methyl-4-(1-methyl-4-(1-methyl-4-(1-methyl-4-(α-chloroacrylamido)imidazole-2-carboxamido)pyrrole-2-carboxamido)pyrrole-2-carboxamido)pyrrole-2-carboxamido)propion-O-methylamidoxime;

(44) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propion-O-methylamidoxime;

(79) 3-(1-methyl-4-(1-methyl-4-(1-methyl-4-(α-bromoacrylamido)imidazole-2-carboxamido)pyrrole-2-carboxamido)pyrrole-2-carboxamido)propion-O-methylamidoxime;

(70) 3-(1-methyl-4-(1-methyl-4-(1-methyl-4-(α-bromoacrylamido)imidazole-2-carboxamido)pyrrole-2-carboxamido)pyrrole-2-carboxamido)propioncianamidine;

(71) 3-(1-methyl-4-(1-methyl-4-(1-methyl-4-(α-bromoacrylamido)imidazole-2-carboxamido)pyrrole-2-carboxamido)pyrrole-2-carboxamido)propion-N-methylamidine;

EXAMPLE 6

3-[1-methyl-4[1-methyl-4[1-methyl-4[1-methyl-3(α-bromoacrylamido)pyrazole-5-carboxamido]yrrole-2-carboxamido]pyrrole-2-carboxamidolpyrrole-2-carboxamido]propionitrile To a solution of 350 mg of 3-[1-methyl-4[1-methyl-4[1-methyl-4-[1-methyl-3(α-bromoacrylamido)pyrazole-5-carboxamido]pyrrole-2-carboxamido]pyrrole-2-carboxamido]pyrrole-2-carboxamido]propionamidine hydrochloride (prepared as reported in WO 90/05196) in 20 ml of DMF, were added 120 mg of succinic anhydride and 165 mg of K₂CO₃. The solution was heated at 60° C. for 3 hours then the solvent evaporated under reduced pressure and the crude residue was purified by flash chromatography (methylene chloride/methanol: 95/5) to yield 150 mg of the title compound as a pale yellow solid.

FAB-MS: m/z, 691 (70, [M+H]$^+$);

PMR (DMSO-d$_6$) δ: 11.02 (s, 1H), 10.48 (s, 1H), 10.00 (s, 1H), 9.92 (s, 1H), 8.21 (m, 1H), 7.35 (s, 1H), 7.30 (d, J=1.8 Hz, 1H), 7.24 (d, J=1.8 Hz, 1H), 7.17 (d, J=1.8 Hz, 1H), 7.09 (d, J=1.8 Hz, 1H), 7.06 (d, J=1.8 Hz, 1H), 6.79 (d, J=3.4 Hz, 1H), 6.31 (d, J=3.4 Hz, 1H), 4.04 (s, 3H), 3.86 (s, 3H), 3.83 (s, 3H), 3.80 (s, 3H), 3.42 (m, 2H), 2.75 (m, 2H).

By analogous procedure and by using the opportune starting materials the following compounds can be obtained:

(17) 3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propionitrile;

(31) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propionitrile;

(40) 3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propionitrile;

(45) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propionitrile;

(58) 3-(1-methyl-4-(1-methyl-4-(l1-methyl-4-(1-methyl-3-(α-bromoacrylamido)pyrazole-5-carboxamido)imidazole-2-carboxamido)pyrrole-2-carboxamido)pyrrole-2-carboxamido)propionitrile;

(69) 3-(1-methyl-4-(1-methyl-4-(1-methyl-3-(α-bromoacrylamido)pyrazole-5-carboxamido)pyrrole-2-carboxamido)pyrrole-2-carboxamido]propionitrile;

(80) 3-(1-methyl-4-(1-methyl-4-(1-methyl-4-(α-bromoacrylamido)imidazole-2-carboxamido)pyrrole-2-carboxamido)pyrrole-2-carboxamido)propionitrile;

EXAMPLE 7

3-[1-methyl-4[1-methyl-4[1-methyl-3(α-bromoacrylamido)pyrazole-5-carboxamido]pyrrole-2-carboxamido]pyrrole-2-carboxamido]propionamide Step I: The Intermediate 3-[1-methyl-4[1-methyl-4[1-methyl-3-aminopyrazole-5-carboxamido]pyrrole-2-carboxamido]pyrrole-2-carboxamido]propionamide hydrochloride To a solution of 200 mg of 3-(1-methyl-4 (1-methyl-4-(1-methyl-3-nitropyrazole-5-carboxamido)pyrrole-2-carboxamido)pyrrole-2-carboxamido)propionamidine hydrochloride (prepared as described in WO 96/05196) in 10 ml of acetonitrile and 10 ml of water, 2 ml of NaOH 1N were added. The solution was heated at 60° C. for 4 hours then the solvent was evaporated in vacuo and the crude residue was purified by flash chromatography (methylene chloride/methanol: 10/1) affording 175 mg of 3-(1-methyl-4(1-methyl-4-(1-methyl-3-nitropyrazole-5-carboxamido)pyrrole-2-carboxamido)pyrrole-2-carboxamido)propionamide as a light yellow solid.

The nitro derivative (170 mg) was dissolved in a mixture of 20 ml of methanol-dioxane-10%hydrochloric acid (4:1:1) and reduced over Pd catalyst (10% on charcoal) under hydrogen pressure (50 psi) into a Parr apparatus. The solution obtained after filtration of the catalyst was evaporated to dryness giving a solid residue which was suspended in dry ethanol, and filtered to yield 150 mg of the intermediate as a white solid.

FAB-MS: 471 m/z, (60, [M+H]$^+$);

PMR (DMSO-d$_6$) δ: 10.48 (s, 1H), 10.20 (s, 3H), 10.00 (s, 1H), 9.92 (s, 2H), 8.20 (m, 1H), 7.35 (s, 1H), 7.30 (d, J=1.8 Hz, 1H), 7.18 (s, 1H), 7.09 (d, J=1.8 Hz, 1H), 4.04 (s, 3H), 3.86 (s, 3H), 3.83 (s, 3H), 3.33 (m, 2H), 2.30 (m, 2H).

By analogous procedure and by using the opportune starting materials the following products can be obtained:

3-[1-methyl-4[1-methyl-4[1-methyl-4-aminoimidazole-4-carboxamido]pyrrole-2-carboxamido]pyrrole-2-carboxamido]propionamide.hydrochloride;

3-[1-methyl-4[1-methyl-4[1-methyl-3-aminopyrazole-5-carboxamido]pyrrole-2-carboxamido]pyrrole-2-carboxamido]propionamide.hydrochloride;

3-[1-methyl-4[1-methyl-4[1-methyl-4-aminopyrrole-4-carboxamido]pyrrole-2-carboxamido]imidazole-2-carboxamido]propionamide.hydrochloride;

3-[1-methyl-4[1-methyl-4[1-methyl-4-aminopyrrole-4-carboxamido]pyrrole-2-carboxamido]pyrrole-2-carboxamido]propion-N-methylamide.hydrochloride;

3-[1-methyl-4[1-methyl-4[1-methyl-3-aminopyrazole-5-carboxamido]pyrrole-2-carboxamido]pyrrole-2-carboxamido]propion-N-methylamide.hydrochloride;

3-[1-methyl-4[1-methyl-4[1-methyl-4-aminopyrrole-4-carboxamido]pyrrole-2-carboxamido]imidazole-2-carboxamido]propion-N-methylamide.hydrochloride.

Step II: The Title Compound.

To a solution of 70 mg of a-bromoacrylic acid in 8 ml of DMF, 50 mg of dicyclohexylcarbodiimide were added. The solution was stirred at room temperature for 20' then added of 110 mg of the intermediate obtained from step I and 18 mg of NaHCO₃. The mixture was stirred at room temperature for 8 hours, the solvent evaporated in vacuo and the crude residue purified by flash chromatography (methylene chloride/methanol: 9/1) to give 70 mg of the title compond as a white solid.

FAB-MS: m/z, 587 (75, [M+H]$^+$);

PMR (DMSO-d$_6$) d: 10.30 (s, 1H), 10.27 (s, 1H), 9.98 (s, 1H), 9.92 (s, 2H), 8.20 (m, 1H), 7.30 (s, 1H), 7.30 (d, J=1.8 Hz, 1H), 7.20 (s, 1H), 7.09 (d, J=1.8 Hz, 1H), 6.66 (d, J=3.0 Hz, 1H), 6.20 (d, J=3.0 Hz, 1H), 4.04 (s, 3H), 3.86 (s, 3H), 3.83 (s, 3H), 3.33 (m, 2H), 2.30 (m, 2H).

By analogous procedure and by using the opportune starting materials the following compounds can be obtained:

(7) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propionamide FAB-MS: m/z 709 (60, [M+H]$^+$);

PMR (DMSO-d$_6$) δ: 11.02 (s, 1H), 10.48 (s, 1H), 10.00 (s, 1H), 9.92 (s, 1H), 9.50 (s, 2H), 8.22 (t, J=5.0 Hz, 1H), 7.35 (s, 1H), 7.31 (d, J=1.7 Hz, 1H), 7.24 (d, J=1.7 Hz, 1H), 7.18 (d, J=1.7 Hz, 1H), 7.09 (d, J=1.7 Hz, 1H), 7.06 (d, J=1.7 Hz, 1H), 6.93 (d, J=1.7 Hz, 1H), 6.80 (d, J=3.2 Hz, 1H), 6.31 (d, J=3.2 Hz, 1H), 4.00 (s, 3H), 3.85 (s, 3H), 3.83 (s, 3H), 3.82 (s, 3H), 3.40 (m, 2H), 2.50 (m, 2H);

(8) 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N-methylamide;

(22) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propionamide;

(23) 3-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propion-N-methylamide FAB-MS: m/z 723 (80, [M+H]$^+$);

PMR (DMSO-d$_6$) δ: 11.54 (s, 1H), 10.12 (s, 1H), 9.96 (s, 1H), 9.92 (s, 1H), 9.40 (m, 1H), 8.25 (m, 1H), 7.52 (s, 1H), 7.26 (d, J=1.7 Hz, 1H), 7.23 (d, J=1.7 Hz, 1H), 7.18 (d, J=1.7 Hz, 1H), 7.15 (d, J=1.7 Hz, 1H), 7.06 (d, J=1.7 Hz, 1H), 6.92 (d, J=1.7 Hz, 1H), 6.80 (d, J=3.0 Hz, 1H), 6.30 (d, J=3.0 Hz, 1H), 3.97 (s, 3H), 3.84 (s, 3H), 3.82 (s, 3H), 3.80 (s, 3H), 3.30 (m, 2H), 3.00 (s, 3H), 2.28 (m, 2H);

(36) 3-(1-methyl-4-(1-methyl-4-(1-methyl-3-(1-methyl-3-(α-bromoacrylamido)pyrazole-5-carboxamido)pyrrole-5-carboxamido)pyrrole-2-carboxamido)pyrrole-2-carboxamido)propion-N-methylamide;

(42) 3-(1-methyl-4-(1-methyl-4-(1-methyl-4-(1-methyl-4-(α-bromoacrylamido)imidazole-2-carboxamido)imidazole-2-carboxamido)pyrrole-2-carboxamido)pyrrole-2-carboxamido)propion-N-methylamide;

(51) 3-(1-methyl-4-(1-methyl-4-(1-methyl-4-(1-methyl-4-(α-bromoacrylarnido)pyrrole-5-carboxamido)pyrrole-2-carboxamido)pyrrole-2-carboxamido)imidazole-2-carboxamido)propionamide;

(74) 3-(1-methyl-4-(1-methyl-4-(1-methyl-4-(α-bromoacrylamido)imidazole-2-carboxamido)pyrrole-2-carboxamido)pyrrole-2-carboxamido)propionamide;

(75) 3-(1-methyl-4-(1-methyl-4-(1-methyl-4-(α-bromoacrylamido)imidazole-2-carboxamido)pyrrole-2-carboxarnido)pyrrole-2-carboxamido)propion-N-methylamide;

(62) 3-(1-methyl-4-(1-methyl-4-(1-methyl-3-(α-bromoacrylamido)pyrazole-5-carboxamido)pyrrole-2-carboxamido)pyrrole-2-carboxamido)propion-N,N'-dimethylamidine;

(63) 3-(1-methyl-4-(1-methyl-4-(1-methyl-3-(α-bromoacrylamido)pyrazole-5-carboxamido)pyrrole-2-carboxamido)pyrrole-2-carboxamido)propion-N,N,N'-trimethylamidine;

(76) 2-(1-methyl-4-(1-methyl-4-(1-methyl-4-(α-bromoacrylamido)imidazole-2-carboxamido)pyrrole-2-carboxamido)pyrrole-2-carboxamido)ethylguanidine;

(77) 3-(1-methyl-4-(1-methyl-4-(1-methyl-4-(α-bromoacrylamido)imidazole-2-carboxamido)pyrrole-2-carboxamido)pyrrole-2-carboxamido)propion-N,N-dimethylamine.

EXAMPLE 8

Intramuscular Injection 10 mg/ml

An injectable pharmaceutical composition was manufactured by dissolving 10 g of 3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N-methylamidine in water for injection (1000 ml) and sealing ampoules of 1–5 ml.

EXAMPLE 9

Capsules, each dosed at 0.200 g and containing 10 mg of the active substance were prepared as follows:

Composition for 500 capsules:

| | |
|---|---|
| 3-(1-methyl-4-(1-methyl-4-(1-methyl-4-(1-methyl-3-(α-bromo acrylamido)pyrazole-5-carboxamido)pyrrole-2-carboxamido) pyrrole-2-carboxamido)pyrrole-2-carboxamido)propion-N-methylamidine hydrochloride | 5 g |
| Lactose | 85 g |
| Corn starch | 5 g |
| Magnesium stearate | 5 g |

This formulation can be encapsulated in two-piece hard gelatin capsules and dosed at 0.200 g for each capsule.

What is claimed is:

1. A compound which is an acryloyl substituted distamycin derivative of formula (I)

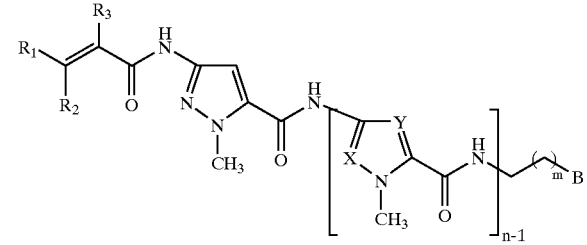

wherein:

n is 2, 3 or 4;

m is 1 or 2;

X and Y are the same or different and are selected, independently for each heterocyclic ring of the polyheterocyclic chain, from N and CH;

$R_1$ and $R_2$ are both hydrogen atoms;

$R_3$ is hydrogen or halogen;

B is selected from

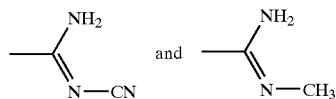

or a pharmaceutically acceptable salt thereof;
provided that
X and Y are not both N for the same heterocyclic ring.

2. A compound according to claim 1 wherein
n is 3 or 4;
m is 1; and
$R_3$ is chlorine or bromine.

3. A pharmaceutical composition comprising one or more pharmaceutically acceptable carriers and/or diluents and, as the active principle, a compound as defined in claim 1.

4. A compound as defined in claim 1 for use in a method of treatment of a human or animal body by therapy.

5. A compound as claimed in claim 4 for use as an antitumour agent.

6. A method of manufacturing a medicament for use as an antitumor agent comprising utilizing a compound as defined in claim 1.

7. A compound selected from the group consisting of:
3-(1-methyl-4-(1-methyl-4-(1-methyl4-(1-methyl-3-(α-bromoacrylamido)-pyrazole-5-carboxamido)pyrrole-2-carboxamido)pyrrole-2-carboxamido)pyrrole-2-carboxamido)propioncyanamidine;
3-(1-methyl-4-(1-methyl-4-(1-methyl-4-(1-methyl-3-(α-bromoacrylamido)pyrazole-5-carboxamido)pyrrole-2-carboxamido)pyrrole-2-carboxamido)pyrrole-2-carboxamido)propion-N-methylamidine;
3-(1-methyl-4-(1-methyl-4-(1-methyl-4-(1-methyl-3-(α-chloroacrylamido)pyrazole-5-carboxamido)pyrrole-2-carboxamido)pyrrole-2-carboxamido)pyrrole-2-carboxamido)propion-N-methylamidine;
3-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propion-N-methylamidine;
3-(1-methyl-4-(1-methyl-4-(1-methyl-3-(1-methyl-3-(α-chloroacrylamido)pyrazole-5-carboxamido)pyrazole-5-carboxamido)pyrrole-2-carboxamido)pyrrole-2-carboxamido)propion-N-methylamidine;
3-(1-methyl-4-(1-methyl-4-(1-methyl-4-(1-methyl-3-(α-bromoacrylamido)pyrazole-5-carboxamido)imidazole-2-carboxamido)pyrrole-2-carboxamido)pyrrole-2-carboxamido)propion-N-methylamidine;
3-(1-methyl-4-(1-methyl-4-(1-methyl-3-(α-bromoacrylamido) pyrazole-5-carboxamido)pyrrole-2-carboxamido)pyrrole-2-carboxamido) propioncyanamidine;
3-(1-methyl-4-(1-methyl-4-(1-methyl-3-(α-bromoacrylamido) pyrazole-5-carboxamido)pyrrole-2-carboxamido)pyrrole-2-carboxamido)propion-N-methylamidine;
3-(1-methyl-4-(1-methyl-4-(1-methyl-3-(α-chloroacrylamido) pyrazole-5-carboxamido)pyrrole-2-carboxamido)pyrrole-2-carboxamido)propion-N-methylamidine; and the pharmaceutically acceptable salts thereof.

8. A process for preparing a compound as defined in claim 1, which process comprises:

(a) reacting a compound of formula:

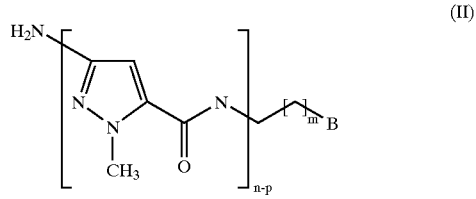

wherein n, m, and B are as defined in claim 1;
p is 0 or 1;
with a compound of formula:

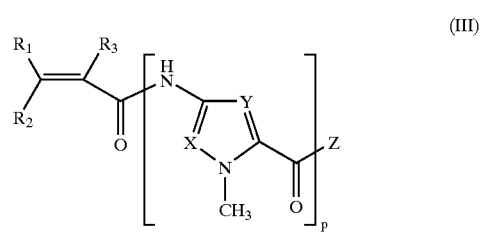

wherein $R_1$, $R_2$, and $R_3$, are as defined in claim 1;
p is as defined above;
z is hydroxy or a leaving group;

or:

(b) when B is equal to —C≡N, reacting a compound of formula:

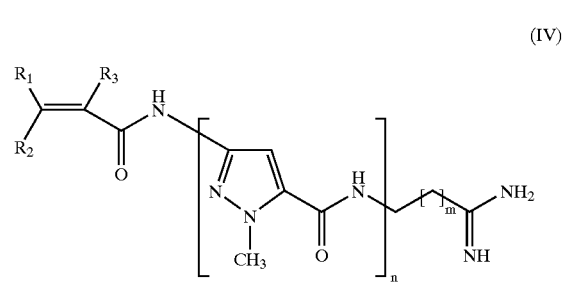

wherein n, m, $R_1$, $R_2$, and $R_3$, are as defined above;
with succinic anhydride; and, (c) if desired, converting a compound of formula (I) into a pharmaceutically acceptable salt thereof.

* * * * *